United States Patent [19]

Kreimer et al.

[11] 4,279,893
[45] Jul. 21, 1981

[54] VACCINE AGAINST NEWCASTLE FOWL DISEASE, METHOD FOR PREPARING AND USE THEREOF

[76] Inventors: July K. Kreimer, Yantarny proezd, 33, kv. 28; Ljubov S. Ageeva, ulitsa Korneichuka, 52, kv. 1, both of Moscow, U.S.S.R.

[21] Appl. No.: 184,933

[22] Filed: Sep. 8, 1980

[30] Foreign Application Priority Data

Oct. 29, 1979 [SU] U.S.S.R. .............................. 2833299

[51] Int. Cl.$^3$ .................... A61K 39/155; A61K 39/17
[52] U.S. Cl. ....................................... 424/89; 435/235
[58] Field of Search ................... 424/89; 435/235-239

[56] References Cited

U.S. PATENT DOCUMENTS

| | | | |
|---|---|---|---|
| 2,767,117 | 10/1956 | Crawley | 424/89 |
| 2,798,835 | 7/1957 | Markham et al. | 424/89 |
| 3,029,190 | 4/1962 | Hanson et al. | 424/89 |
| 3,060,094 | 10/1962 | Dutcher et al. | 424/89 |
| 3,548,054 | 12/1970 | Bowen et al. | 424/89 |
| 3,674,864 | 7/1972 | Angelucci | 424/89 |
| 3,876,763 | 4/1975 | Yoshikazu et al. | 424/89 |
| 4,053,583 | 10/1977 | Gits et al. | 424/89 |
| 4,071,618 | 1/1978 | Knobe et al. | 424/89 |
| 4,235,876 | 11/1980 | Gits et al. | 424/89 |

OTHER PUBLICATIONS

Ageeva, L. S. et al., Trudy Gosudarsrvennoso Nauchno-Kontrol'noso Instituta Veterinarnykh Preparatov, 1971, 17, 24-34, Biological Properties of Lentogenic Strains of Newcastle Disease Virus.
Serebryakov, A. S. Veterinariya (Moscow), No. 8, 68-70 (1972), Aerosol Immunization of Chicks Against Newcastle Disease.
Allan, W. H. et al., Newcstle Disease Vaccines their Production and Use, 163 p. 1978, Rome, Italy, Food and Agriculture Organization of the United Nations, ISBN 92-5-100484-6.
Alexander, D. J. et al., Res. Vet. Sci. (1979), 26.2, 198-201, Resistance of Chickens to Challenge with the Virulent Herts 33 Strain Newcastle Disease Virus, with Serologically Distinct Avian Paramyxoviruses.
Alexander, D. J. et al., Arch. Virol. 60 (2), 105-113 (1979), Properties of a Newly Isolated Serologically Distinct Avian Paramyxovirus.
Kreimer, Iukh et al., Veterinariya (Mosk), 8, 47-49, Aug. 1975, Cutaneous-Follicular Method of Chick Vaccination Against Newcastle Disease and Smallpox.
Alexander, A. J., Arch. Gesamte Virusforsch., 74:46 (3-4), 291-301, Comparison of the Structural Polypeptides of Four Avian Paramyxoviruses.
Shortridge, K. F. et al., J. Gen. Virol, 49 (PT. 2):255-262, Aug. 1980, Isolation and Properties of Viruses from Poultry in Hong Kong which Represent a New (Sixth) Distinct Group of Avian Paramyxo Viruses.

Primary Examiner—Shep K. Rose
Attorney, Agent, or Firm—Steinberg & Raskin

[57] ABSTRACT

The vaccine against Newcastle fowl disease incorporates a virus-containing extra-embryonic liquid of a lentogenic strain Paramyxovirus a-1 "Bor-74 VGNKI" deposited at the All-Union State Research and Control Institute for Veterinary Preparations of the USSR Ministry of Agriculture and has a biological acitivity of from $10^{8.0}$ to $10^{9.75}$ EID$_{50}$/ml.

The method for preparing this vaccine comprises infectioning chicken embryos with the strain Paramyxovirus a-1 "Bor-74 VGNKI", preparation of a matrass breeding culture of the virus at the temperature of 37°-37.5° C. for 72-80 hours followed by isolation of the virus-containing extra-embryonic liquid and manufacture of the vaccine. The vaccine is employed for prophylaxis of Newcastle fowl disease by way of administration thereof once or twice onto mucous membrane of the fowl eye or nose in a dose of from 0.05 to 1.0 ml at the dilution of 1:100 or by way of enteral administration with potable water to chicks of an age of up to 25 days in a single dose of from 7.5 to 10 ml at the dilution of 1:1,000, followed by revaccination of the elder fowl, or by administration as an aerosol to the fowl of an age under 25 days in a dose of 300-400 EID$_{50}$, followed by revaccination of the elder fowl in a dose of from 800 to 1,000 EID$_{50}$.

12 Claims, No Drawings

VACCINE AGAINST NEWCASTLE FOWL DISEASE, METHOD FOR PREPARING AND USE THEREOF

FIELD OF THE INVENTION

The present invention relates to veterinary and, more specifically, to a novel vaccine against Newcastle fowl disease and a method for preparing same, as well as to application of the novel vaccine in prophylaxis of Newcastle fowl disease.

BACKGROUND OF THE INVENTION

Newcastle fowl disease (pseudoplague, atypic plague, Asian plague, avain pneumoencephalitis) is a virus acute infection disease occurring in the form of epizootia and causing mass death of perceptible fowl. Newcastle fowl disease is the most widespread infection throughout the globe; it brings about a high economic damage to the national economies and pertains to dangerous infections. Control of Newcastle fowl disease is an urgent and important portion of the program of the fight against infectional diseases of animals and fowl.

At the present time, the foci of infection of Newcastle fowl disease are eliminated by the total slaughter of ill and suspected fowl.

Known in the art are various inactivated and virus-vaccines for specific prophylaxis of Newcastle fowl disease. Inactivated vaccines are prepared by inactivation of a virus-containing extra-embryonic liquid with formalin or betapropiolactone. The basic disadvantages thereof reside in a low immunogeneity, high production costs and the necessity of individual treatment of fowl by injection.

Known are virus-vaccines employed for specific prophylaxis of Newcastle fowl disease which are classified into two groups: lentogenic avirulent (strains $B_1$, La-Sota, F) and mesogenous with the residual virulence (strains Roakin, Komarova, H). Dry virus-vaccines consist of a virus-containing extra-embryonic liquid and a protective medium. As the protective medium use is made mainly of defatted milk ("Partial Veterinary Virusology", Moscow, "Kolos" Publishing House, p. 233-240).

The main disadvantage of the virus-vaccine pertaining to the group of mesogenous strains is the presence of a residual virulence, wherefore they have a limited application. Virus-vaccines of strains "$B_1$" and "F" are weakly immunogenic, while the vaccine of the strain "H" have a residual reactogeneity for fowl.

Among currently known vaccines, the most pronounced immunogeneity is inherent in the vaccine of the strain "La-Sota". This vaccine consists of 50% of virus-containing extra-embryonic liquid of the strain "La-Sota", 50% of the protective medium and antibiotics. The vaccine of the strain "La-Sota" is harmless; when administered intranasally, it is used in the volume of 0.1 ml at the dilution of 1:25; at enteral administration with potable water for two days in a volume of 5 to 15 ml at the dilution of 1:500; at aerosol administration in doses of 600 to 1,200 $EID_{50}$.

The method for preparing vaccine from the strain "La-Sota" consists in the following: chicken embryos are infected with the virus in the volume of 0.1 ml at the dilution of $10^{-3}$, matrass breeding of the virus with an activity of at least $10^{7.5}$ $EID_{50}$/ml is effected for 96-120 hours, then the recovered virus-containing extra-embryonic liquid is mixed with the protective medium, packed, lyophilized and the final vaccine is checked. This vaccine for the prophylaxis purposes is used, as it has been mentioned hereinabove, intranasally, as aerosol, and enterally with potable water. However, the use of the vaccine is effected repeatedly. Thus, fowl of an up to 150 days' age is vaccinated with this virus-vaccine three times and then every 6 months. Despite repeated vaccination with this vaccine, in numerous fowl-breeding farms there occur breakage of immunity and fowl death because of Newcastle disease.

SUMMARY OF THE INVENTION

It is the main object of the present invention to provide a vaccine against Newcastle fowl disease which would be harmless and possess an increased immunogeneity.

It is another object of the present invention to provide a method for preparing vaccine against Newcastle fowl disease which would have a shortened process cycle of its manufacture.

The main and other objects of the invention are accomplished by a vaccine against New-castle fowl disease containing a virus-containing extra-embryonic liquid of the Newcastle fowl disease virus, wherein, according to the present invention, as the virus-containing extra-embryonic liquid of the Newcastle fowl disease virus it contains the virus-containing extra-embryonic liquid of the strain Paramyxovirus a-1 "Bor-74 VGNKI" deposited at the All-Union State Research and Control Institute for Veterinary Preparations of the USSR Ministry of Agriculture and has biological activity of from $10^{8.0}$ to $10^{9.75}$ $EID_{50}$/ml.

The vaccine can be produced both in a liquid and dry form. For the production of a dry vaccine, it is advisable to introduce a protective medium-defatted milk in an equal proportion with the virus-containing extra-embryonic liquid. The vaccine can also incorporate antibiotics in an amount of from 100 to 200 ED per 1 ml of the vaccine. As the antibiotics the vaccine preferably contains penicillin and streptomycin. The present invention also provides the method for preparing this vaccine.

In the method for preparing the vaccine according to the present invention against Newcastle fowl disease involving infectioning of chicken embryos with the virus of Newcastle disease, preparation of the matrass breeding culture of the virus with isolation of the virus-containing extra-embryonic liquid and production of the vaccine, in accordance with the present invention, as the virus of Newcastle fowl disease use is made of the strain Paramyxovirus a-1 "Bor-74 VGNKI" and the preparation of the matrass breeding culture of the virus is effected for a period of from 72 to 80 hours at the temperature of 37.0°-37.5° C. It is advisable that said infectioning of chicken embryos be effected using the strain Paramyxovirus 1-a "Bor-74 VGNKI" with a dose of from $10^{4.0}$ to $10^{5.0}$ $EID_{50}$/0.1 ml.

The preparation of the dry vaccine is effected by mixing the isolated virus-containing extra-embryonic liquid with the protective medium, followed by packing and lyophilization. As the protective medium use is made of defatted milk which is employed in the equal proportion relative to the virus-containing extra-embryonic liquid. Prior to packing of the vaccine, with the view to avoid its possible contact with a foreign microflora, antibiotics can be added thereto in an amount of 100-200 ED per 1 ml of the vaccine. The resulting vaccine is harmless and featuring a high immunogeneity. The vaccine according to the present invention is employed for prophylactic purposes for vaccination of perceptible fowl of all age groups.

In accordance with the present invention, the mode of prophylaxis of Newcastle fowl disease consists in that the vaccine according to the present invention is administered to fowl nasal or eye mucous membrane in a dose of from 0.05 to 0.1 ml at the dilution of 1:100 once or twice. The vaccine can be administered either enterally (per os with potable water) to chicks of an age of up to 25 days in a single dose of from 7.5 to 10 ml at the dilution of 1:1,000, followed by revaccination of fowl of an elder age in a single dose of from 10 to 15 ml at the dilution of 1:1,000. The vaccine can be introduced as aerosol to fowl of an age of up to 25 days in a dose of 300–400 $EID_{50}$, followed by revaccination of elder fowl in a dose of from 800 to 1,000 $EID_{50}$.

DETAILED DESCRIPTION OF THE INVENTION

For the preparation of the vaccine according to the present invention use is made of the strain Paramyxovirus a-1 "Bor-74 VGNKI" isolated from chicks under natural conditions which possesses the following properties:

Morphological features:

Observation in an electron microscope shows aggregations and individual particles, mainly of thread-like and racket-like forms of virions, as well as spherical and polymorphic particles of this virus.

The virion shell is covered with a number of fine filament-like projections with a length of 80–100 Å and diameter about 30 Å. They are extending above the shell surface and spaced from one another by 70–80 Å. In thread-like forms of virions such filament-like projections are disposed over the shell in regular or uniform rows.

In the employed preparations of the strain Paramyxovirus a-1 "Bor-74 VGNKI" there are present mainly intact forms of virions. By this property the strain differs from other vaccine strains ($B_1$, La-Sota and F) and the virus of Newcastle fowl disease containing also semi-damaged and damaged virions.

In certain preparations of the strain Paramyxovirus a-1 "Bor-74 VGNKI" there is found a fine filamentous helical structure with a regular periodicity of 50 Å along its axis. Its diameter is about 170 Å, diameter of the central channel is 40–50 Å. This structure is the virus ribonucleoprotein. It is similar to the structure of other strains of the Newcastle fowl disease virus.

For the strain "Bor-74 VGNKI" features a smaller, as compared to strains "La-Sota, "$B_1$" and "F", amount of spherical forms of virions (with a size of from 90 to 150 nm). Comparatively larger was the number of thread-like forms of virions with a diameter of 100–150 nm and length of 1.5 nm. Racket-like forms of virions have been less frequently encountered.

Cultural properties:

The virus is cultured in 9–10 days' chicken embryos without causing their death for 96 hours' incubation at the temperature of 37° C. Thermostable.

Perceptibility: Chicken embryos and all age groups of fowl are perceptive to the virus of the strain Paramyxovirus a-1 "Bor-74 VGNKI".

Virulent and antigenous properties:

The strain Paramyxovirus a-1 "Bor-74 VGNKI" is avirulent for fowl of all age groups. Pertains to the group of lentogenic strains.

Possesses a pronounced ability of conservation in nature. Capable of being transferred by natural ways. Causes, in perceptible fowl, the formation of specific antibodies inhibiting hemagglutination and neutralizing the virus of standard strains of the Newcastle fowl disease.

The virus reacts with antibodies produced for homologues and other strains of the Newcastle fowl disease.

When administered to perceptible fowl, it causes the formation of intense immunity against the epizootic virus of Newcastle disease.

Biological activity of the virus is $10^{8.5}–10^{9.75}$ $EID_{50}$/ml

Immunogenic activity (50%):

upon administration onto mucous membrane of fowl nose or eye—2.93 lg $EID_{50}/0.1$ ml;

upon administration per os with potable water—4.97 lg $EID_{50}/10$ ml;

upon aerosol mode of administration to chicks of up to 25 days' age—300–400 $EID_{50}$ and to adult fowl—80-0–1,000 $EID_{50}$.

Perceptible chicks once vaccinated with the strain Paramyxovirus a-1 "Bor-74 VGNKI" onto the fowl nose and eye mucous membrane and by enteral mode of administration were immune 7 days after the vaccination and remained immune for 438 days in 100% of the cases (observation period).

Serological properties:

The virus of the strain Paramyxovirus a-1 "Bor-74 VGNKI" possesses the ability of agglutinate erythrocytes of fowl and animals. It provides a pronounced spontaneous agglutination with RBC of chicken embryos. The hemagglutinating titre is 1:512. The agglutination reaction is fine-grained and slowly revealed.

The method for the preparation of the vaccine resides in the following.

Chicken embryos free from antibodies against the virus of Newcastle disease and other avian diseases are infected with the strain Paramyxovirus a-1 "Bor-74 VGNKI". The production lot of the virus is prepared from a matrass breeding culture of the virus. The suspension of the virus of the strain Paramyxovirus a-1 "Bor-74 VGNKI" in a dose of from $10^{4.0}$ to $10^{5.0}$ $EID_{50}/0.1$ ml is used to infect the chicken embryos into the allantois cavity. The infected embryos are incubated at a temperature of 37.0–37.5° C. for 72–80 hours. Then the recovered virus-containing extra-embryonic liquid is collected under sterile conditions. In the preparation of a liquid vaccine the thus-prepared liquid is packed and checked for sterility, biological activity, harmlessness and immunogeneity. In the preparation of a dry vaccine the recovered liquid is mixed in equal proportions with a protective medium, e.g. sterile defatted milk, and poured in ampules (flasks) then lyophilized and each lot is checked for the residual moisture, sterility, biological activity, harmlessness and immunogeneity. The resulting vaccine is harmless for all age groups of fowl, it features high immunogeneity and makes it possible to reduce the number of vaccinations.

The method for the vaccine preparation differs from the prior art methods for the preparation of known vaccines by a reduced process cycle (duration of 72–80 hours instead of 96–120 hours as in the prior art method).

At the present time the vaccine according to the present invention has been tested in fowl-breeding farms with 7 mln of species and positive results have been obtained.

For a better understanding of the present invention, some specific examples illustrating preparation of the vaccine against Newcastle fowl disease and use thereof for prophylaxis of this disease are given hereinbelow.

EXAMPLE 1

For the preparation of three test series of dry virus-vaccine from the strain Paramyxovirus a-1 "Bor-74 VGNKI" use is made of 10-days embryos of chicken free from antibodies against the virus of Newcastle disease and other fowl diseases. For each series of the vaccine use is made of 300 embryos. Series No. 1 has the starting biological activity of $10^{8.50}$ EID$_{50}$/ml, Series No. 2—$10^{8.75}$ EID$_{50}$/ml and Series No. 3 has the starting biological activity of $10^{9.50}$ EID$_{50}$/ml.

The production lot of the virus of the strain Paramyxovirus a-1 "Bor-74 VGNKI" is prepared from the lyophilized matrass breeding culture of the 10th passage. The virus suspension at the dilution of $10^{-4}$ is used to infect embryos into the allantoic cavity in the volume of 0.1 ml. The infected and control embryos are incubated at the temperature of 37° C. for 72 hours. For the preparation of the vaccine use is made of only live embryos of the 72-hours' incubation which are preliminary cooled at the temperature of $+4°$ C. for at least 8 hours.

The number of dead infected and control chicken embryos for the incubation period of 72 hours is shown in Table 1.

TABLE 1

| | | Death of infected chicken embryos for 72 hours (three experiments) | | | | |
|---|---|---|---|---|---|---|
| | | Died after | | | Died, total | |
| No. | Number of embryos | after 24 hours | 48 hours | 72 hours | Number | % |
| 1 | 900 (test) | 48 | 9 | 3 | 60 | 6.7 |
| 2 | 36 (control) | — | — | — | — | — |

It is seen from Table 1 that the death of infected embryos for the incubation period of 72 hours was about 6.7%. Therewith, the basic number of died embryos was observed within the first 24 hours after infection (i.e. non-specific death).

For the preparation of the vaccine use is made of only sterile, both bacterially and fungally, allantoic and amniatic liquid which is poured into the same vessel under sterile conditions, mixed in equal (by volume) proportions with sterile defatted milk and poured into ampules of 4 ml capacity. Then the vaccine is lyophilized. The ampules are sealed in vacuum collectors. The ampules with the vaccine without vacuum are discarded. All the ampules are labeled with the label bearing information showing the name of the biopreparation, lot No. and the date of manufacture.

Every test lot of the vaccine is checked for the residual moisture, sterility, harmlessness and immunogeneity.

The analysis of the native and dry vaccine for sterility relative to the bacterial and fungal flora is effected by inoculation onto the nutrient media MPA, MPB, MPPB and Saburo medium. The assessment of the inoculation results is effected within 10 days.

Harmlessness is tested on 17-20 days' perceptible chicks by intramuscular injection of the vaccine in the volume of 0.2 ml at the dilution of 1:10. Observation over the chicks is carried out for 14 days. The resulting vaccine should be harmless.

Immunogeneity of the vaccine is determined on 17-20 days' chicks by way of administration onto mucous membrane of the fowl nose or eye (portions of 0.1 ml at the dilution of 1:100 and 1:1,000) and per os with potable water (by portions of 10 ml at the dilution of 1:1,000 and 1:5,000).

The presence and intensity of the immunity in all chicks of both test and control groups are checked 14 days after the vaccination by way of infectioning with the virulent strain "T" of the virus of Newcastle disease in the dose of 1,000 LD$_{50}$/0.2 ml. Observation over the infected fowl is effected for 10 days.

All of the test chicks vaccinated by the above-specified methods after the control infection with the virulent strain "T" of the Newcastle disease virus proved to be immune at the 100% death of the control fowl. The results of the immunogeneity tests are shown in Table 2 hereinbelow.

The determination of a 50% immunizing activity of the dry virus-vaccine from the strain Paramyxovirus a-1 "Bor-74 VGNKI" is effected in six experiments on 17-20 days' chicks using the method of vaccination onto mucous membrane of the fowl nose and enteral vaccination method at a dilution of the virus of from $10^{-4}$ to $10^{-8}$.

Using statistic methods of the data processing, there is determined the immunizing activity (IMD$_{50}$) for each series of the vaccine upon vaccination onto the fowl nose or eye mucous membrane and enteral way of immunization.

The immunizing activity is as follows:

Series No. 1 with the starting biological activity of $10^{8.5}$ EID$_{50}$/ml: upon vaccination onto mucous membrane of the fowl nose mucous membrane was 3.6 lg EID$_{50}$/0.1 ml; in enteral vaccination—5.2 lg EID$_{50}$/10.0 ml;

Series No. 2 with the starting biological activity of $10^{8.75}$ EID$_{50}$/ml was 2.3 lg EID$_{50}$/0.1 ml and 5.0 lg EID$_{50}$/10.0 ml respectively;

Series No. 3 with the starting biological activity of $10^{9.5}$EID$_{50}$/ml: upon the application onto the fowl nose or eye mucous membrane was 2.8 lg EID$_{50}$/0.1 ml, while upon the enteral administration it was 4.7 lg EID$_{50}$/10.0 ml.

As calculated from the results of six experiments, the 50% immunizing activity (IMD$_{50}$) upon vaccination onto the fowl nose mucous membrane was about 2.93 lg EID$_{50}$/0.1 ml and upon the enteral administration—4.97 lg EID$_{50}$/10.0 ml. The test results are shown in Table 3 hereinbelow.

EXAMPLE 2

Testing at fowl-breeding farms of the vaccine according to the present invention from the strain Paramyxovirus a-1 "Bor-74 VGNKI" is carried out in the following manner.

In the tests use is made of:

dry virus-vaccine against Newcastle disease from the strain Paramyxovirus a-1 "Bor-74 VGNKI", series 1, 2 and 3 prepared in Example 1, dry virus-vaccine against Newcastle disease from the strain "La-Sota", control virulent strain "T" of the virus of Newcastle disease. The infection activity is $10^{7.5}$ LD$_{50}$/0.2 ml.

In immunization by the method of application, onto the fowl nose mucous membrane, of the vaccine from the strain Paramyxovirus a-1 "Bor-74 VGNKI", the latter is diluted in the ratio of 1:100, and the vaccine of the strain "La-Sota"—in the ratio of 1:25. The diluted vaccine is dropped into nose (2 drops). Prior to vaccination water was refused and watering of the fowl was effected 1.5 hours after the immunization. Upon immunization of the fowl by the enteral method (per os with potable water) the vaccine of the strain Paramyxovirus a-1 "Bor-74 VGNKI" is diluted at the ratio of 1:1,000 and that of "La-Sota"—1:500. The diluted vaccine is administered to the fowl for one watering at the rate of 10 ml per chick of up to 25 days' age. The watering is effected at once, in the morning, with preliminary refusal in water to the fowl for 8 hours. Water and feedstuff were given to the fowl 1.5 hours after the administration of the vaccine. Prior to the experiment, in all chicks of the entire test lots (25 specimens in each) the level of the passive immunity was determined. The presence of antihemagglutinines in the fowl blood serum was determined in the reaction of delay of hemagglutination with a 4-fold dose of an antigene. The test groups of chicks were vaccinated in the following manner: for the 1st time—at 12–15 days' age; 2nd time—particular revaccination period was determined by the state of intensity of the active immunity 14 days after the first immunization. The presence and level of the active immunity with the fowl injected with the vaccine of the strain Paramyxovirus a-1 "Bor-74 VGNKI" was determined 7, 10, 14, 21 and 42 days after the first vaccination and 14 days after the second vaccination; at the same time, for the fowl injected with the vaccine of the strain La-Sota—on the 14th day after the first and the second vaccinations (25 test specimens after each). The control infection of the test and control groups was effected by intramuscular injection of the virulent strain "T" of the Newcastle fowl disease virus in the dose of 1,000 $LD_{50}/0.2$ ml.

TABLE 2

Results of immunogeneity tests with experimental series of the dry vaccine of the strain Paramyxovirus a-1 "Bor-74 VGNKI"

| Vaccine dilution | Mode of administration | Volume, ml | Number of vaccinated chicks | Control infection results number | out of which died | survived |
|---|---|---|---|---|---|---|
| 1:10 | intramuscularly | 0.2 | 15 | 15 | 0 | 15 |
| 1:100 | nose muccus membrane | 0.1 | 30 | 30 | 0 | 30 |
| 1:1,000 | nose muccus membrane | 0.1 | 30 | 30 | 0 | 30 |
| 1:1,000 | per os with potable water | 10.0 | 30 | 30 | 0 | 30 |
| 1:5,000 | per os with potable water | 10.0 | 30 | 30 | 0 | 30 |
| Control chicks | (non-vaccinated) | — | — | 30 | 30 | 0 |

TABLE 3

Results of determination of a 50% immunizing dose for three series of the vaccine of the strain Paramyxovirus a-1 "Bor-74 VGNKI"

| Dilution | Mode of administration | Volume ml | Number of chicks | Number of chicks | Control infection results out of which: died | survived |
|---|---|---|---|---|---|---|
| 1 | 2 | 3 | 4 | 5 | 6 | 7 |
| $10^{-4}$ | | 0.1 | 15 | 15 | 0 | 15 |
| $10^{-5}$ | on | 0.1 | 15 | 15 | 3 | 12 |
| $10^{-6}$ | nose mu- | 0.1 | 15 | 15 | 8 | 7 |
| $10^{-7}$ | cous membrane | 0.1 | 15 | 15 | 15 | 0 |
| $10^{-8}$ | on nose mucous membrane | 0.1 | 15 | 15 | 15 | 0 |
| $10^{-4}$ | Enteral | 10.0 | 15 | 15 | 0 | 15 |
| $10^{-5}$ | | 10.0 | 15 | 15 | 3 | 12 |
| $10^{-6}$ | | 10.0 | 15 | 15 | 9 | 6 |
| $10^{-7}$ | | 10.0 | 15 | 15 | 12 | 3 |
| $10^{-8}$ | | 10.0 | 15 | 15 | 15 | 0 |
| Control (non-vaccinated) chicks | | — | 30 | 30 | 30 | 0 |

The infected fowl was subjected to observation over 10 days. Chicks of the test series were all weighed at the 60 days' age and their average weight was determined.

At the farm there have been tested:

the method of vaccination by way of administration of the vaccine onto mucous membrane of the fowl nose or eye (13 production lots—total of 188, 300 species);

enteral method of vaccination (3 production lots—total of 40,400 species);

aerosol vaccination method (27 production lots—more than 600,000 species).

All of the fowl lots were subjected to a permanent observation and autopsy of the died fowl was effected every day. In none of the test lots of chicks vaccinated by the above-specified methods of administration of the vaccine of the strain Paramyxovirus a-1 "Bor-74 VGNKI" there was noticed any visible external reaction on to the introduced antigen. The chicks were mobile, actively ate the food-stuff and developed normally. The post-vaccination response (suppression, hindered breathing, rale) was observed on the 4-6-th day in the chicks primarily vaccinated by the aerosol method with the vaccine of the strain Paramyxovirus a-1 "Bor-74 VGNKI" and on the 6-8 day—in the chicks vaccinated with the vaccine of the strain "La-Sota". The response to the introduction of the vaccine of the strain "La-Sota" was clinically pronounced slightly more clearly than that to the vaccine of the strain Paramyxovirus a-1 "Bor-74 VGNKI". The titre of antibodies in the chicks vaccinated by the above-described methods of administration of the vaccine of the strain Paramyxovirus a-1 "Bor-74 VGNKI" 7, 10 and 14 days after the vaccination was noticeably increased and by the 21st day it was within the range of from 6.1 to 7.4 $\log_2$. The titre of antibodies was more pronounced in the chicks vaccinated by the aerosol and enteral methods of administration of the vaccine.

The control infection was effected in 17 test groups of the fowl including:

one group (10 species) non-vaccinated, set up for the contact vaccination, survived in 100% of the cases;

three groups (100 species) vaccinated by the enteral method survived in 100% of cases;

4 groups (80 species) vaccinated by administration onto the fowl eye or nose mucous membrane survived in 100% of cases;

9 groups (135 species) vaccinated by the aerosol method survived in 97.8% of the cases.

All the control groups (50 species)—non-vaccinated chicks—died from Newcastle disease.

Keeping ratio at the farm of chicks of from 10 to 60-days age was within the range of from 96.9 to 98.3%; an average bodyweight gain of youngsters of 1 to 60 days age was 10.0–10.4 g. Observations carried out for 6 months over the chicks vaccinated with the dry virus-vaccine of the strain Paramyxovirus a-1 "Bor-74 VGNKI" have shown its harmlessness and a high immunogeneity.

There was effected the determination of the time of origination and duration of immunity in the fowl vaccinated with the dry virus-vaccine of the strain Paramyxovirus a-1 "Bor-74 VGNKI". The time of occurrence and duration of immunity in the chicks vaccinated once by the method of administration of the vaccine onto the fowl mucous membrane of eye and by the enteral method of administration of the vaccine according to the present invention was determined. In the experiment use was made of 300 perceptible chicks of the 35 days' age. Out of them 150 chicks were vaccinated by the method of application, onto the fowl nose mucous membrane, of the vaccine in the volume of 0.1 ml at the dilution of 1:100, and 150 chicks were vaccinated by the enteral method in a single dose of 7.5 ml at the dilution of 1:1,000 per chick. The control lot was composed of 65 non-vaccinated fowl. The immunity was tested 7, 10, 14, 31, 84, 112, 148, 178, 204, 235, 287, 350 and 438 days (observation period) after the single vaccination by way of the determination of the level of specific antihemagglutinines in blood serum and by control infection with the virulent strain "T" of the virus of Newcastle disease in the dose of 1,000 $LD_{50}/0.2$ ml. Observation of the infected fowl was effected for 10 days. All the died chicks were subjected to autopsy. The results of the thus-made investigations are shown in Table 4. From the data of this Table 4 follows that the chicks vaccinated with the dry virus-vaccine from the strain Paramyxovirus a-1 "Bor-74 VGNKI" by the above-mentioned method of vaccination 7 days after the vaccination and for 438 days were immune in 100%, while all the control chicks died.

It should be noted that in addition to humoral immunity the vaccine according to the present invention forms a clearly pronounced cell immunity. This is evidenced by the fact that the fowl above the 204 days age, despite the low level of specific antibodies (1:4) proved to be imperceptible to the control infection by the virulent strain "T" of the virus of Newcastle fowl disease.

TABLE 4

Immunity after a single-time vaccination of 35-days-aged chicks with the vaccine of the strain Paramyxovirus a-1 "Bor-74 VGNKI"

| Days after vacci- nation | Intranasal vaccination method | | | | Enteral vaccination method | | | |
|---|---|---|---|---|---|---|---|---|
| | titre of antibodies ($\log_2$) | bio test | | | titre of antibodies ($\log_2$) | bio test | | |
| | | number of chicks | out of which: | | | number of chicks | out of which: | |
| | | | died | survived | | | died | survived |
| 7 | 1:16–1:64 (5,0) | 10 | 0 | 10 | 1:16–1:64 (5,2) | 10 | 0 | 10 |
| 10 | 1:64–1:256 (7,0) | 10 | 0 | 10 | 1:128–1:256 (7,6) | 10 | 0 | 10 |
| 14 | 1:128–1:512 (7,9) | 10 | 0 | 10 | 1:128–1:512 (8,3) | 10 | 0 | 10 |
| 31 | 1:128–1:512 (7,8) | 10 | 0 | 10 | 1:128–1:512 (8,1) | 10 | 0 | 10 |
| 84 | 1:64–1:128 (6,4) | 10 | 0 | 10 | 1:64–1:256 (6,6) | 10 | 0 | 10 |
| 112 | 1:16–1:64 (5,2) | 10 | 0 | 10 | 1:32–1:128 (5,5) | 10 | 0 | 10 |
| 148 | 1:8–1:64 (4,9) | 10 | 0 | 10 | 1:16–1:64 (5,1) | 10 | 0 | 10 |
| 178 | 1:8–1:32 (4,0) | 10 | 0 | 10 | 1:8–1:64 (4,3) | 10 | 0 | 10 |
| 204 | 1:4–1:16 (3,8) | 10 | 0 | 10 | 1:8–1:32 (4,0) | 10 | 0 | 10 |
| 235 | 1:4–1:16 (3,7) | 10 | 0 | 10 | 1:4–1:32 (3,8) | 10 | 0 | 10 |
| 287 | 1:4–1:16 (3,6) | 10 | 0 | 10 | 1:4–1:16 (3,7) | 10 | 0 | 10 |
| 350 | 1:4–1:16 | 10 | 0 | 10 | 1:4–1:16 | 10 | 0 | 10 |

TABLE 4-continued

Immunity after a single-time vaccination of 35-days-aged chicks with the vaccine of the strain Paramyxovirus a-1 "Bor-74 VGNKI"

| Days after vacci-nation | Intranasal vaccination method | | | | Enteral vaccination method | | | |
| --- | --- | --- | --- | --- | --- | --- | --- | --- |
| | titre of antibodies ($\log_2$) | bio test | | | titre of antibodies ($\log_2$) | bio test | | |
| | | number of chicks | out of which: | | | number of chicks | out of which: | |
| | | | died | survived | | | died | survived |
| 438 | (3,5) 1:2–1:8 (2,8) | 10 | 0 | 10 | (3,6) 1:2–1:16 (2,9) | 10 | 0 | 10 |
| | Control (non-vaccinated) chicks | | | | | 65 | 65 | 0 |

What is claimed is:

1. A vaccine against Newcastle fowl disease comprising a virus-containing extra-embryonic liquid of a lentogenic strain Paramyxovirus a-1 "Bor-74 VGNKI" deposited at the All-Union State Research and Control Institute for Veterinary Preparations of the USSR Ministry of Agriculture and having its biological activity within the range of from $10^8$ to $10^{9.75}$ $EID_{50}$/ml.

2. A vaccine as claimed in claim 1, wherein a protective medium, i.e. defatted milk, is employed in an equal proportion relative to the virus-containing extra-embryonic liquid.

3. A vaccine as claimed in claim 1, wherein antibiotic are present in an amount of from 100 to 200 ED per ml of the vaccine.

4. A vaccine according to claim 3, wherein as the antibiotic penicillin and streptomycin are employed.

5. A method for preparing a vaccine against Newcastle fowl disease according to claim 1, comprising infectioning chicken embryos with the strain Paramyxovirus a-1 "Bor-74 VGNKI", preparation of a matrass breeding culture of the virus at the temperature of 37.0°–37.5° C. for a period of from 72 to 80 hours, followed by isolation of the virus-containing extra-embryonic liquid and production of the vaccine.

6. A method as claimed in claim 5, wherein infectioning of chicken embyros is effected using the strain Paramyxovirus a-1 "Bor-74 VGNKI" in a dose of from $10^{4.0}$ to $10^{5.0}$ $EID_{50}$/ml.

7. A method as claimed in claim 5, wherein the manufacture of a dry vaccine is effected by mixing the isolated virus-containing extra-embryonic liquid with a protective medium, followed by packing and lyophilization.

8. A method as claimed in claim 7, wherein as the protective medium defatted milk is employed which is taken in an equal proportion relative to the virus-containing extra-embryonic liquid.

9. A method according to claim 5, wherein prior to packing of the vaccine, antibiotics are added thereto in an amount of from 100 to 200 ED per ml of the vaccine.

10. A method of prophylaxis of Newcastle fowl disease comprising administration of the vaccine as claimed in claim 1 onto mucous membrane of the fowl eye or nose in a dose of from 0.05 to 0.1 ml at the dilution of 1:100 once or twice.

11. A method of prophylaxis of Newcastle fowl disease comprising administration of said vaccine as claimed in claim 1 enterally with potable water to chicks of an age of up to 25 days in a dose of from 7.5 to 10 ml at the dilution of 1:1,000 in a single portion, followed by revaccination of the elder fowl in a single dose of from 10 to 15.0 ml at the dilution of 1:1,000.

12. A method of prophylaxis of Newcastle fowl disease comprising administration of said vaccine as claimed in claim 1 as aerosol to the fowl of an age of up to 25 days in a dose of from 300 to 400 $EID_{50}$, followed by revaccination of the elder fowl in a dose of from 800 to 1,000 $EID_{50}$.

* * * * *